United States Patent
Fukuda et al.

(10) Patent No.: US 11,360,017 B2
(45) Date of Patent: Jun. 14, 2022

(54) BIOLOGICAL SAMPLE IMAGING DEVICE AND BIOLOGICAL SAMPLE IMAGING METHOD

(71) Applicant: SYSMEX CORPORATION, Kobe (JP)

(72) Inventors: Masakazu Fukuda, Kobe (JP); Toshikuni Suganuma, Kobe (JP); Kazuhiro Kanou, Kobe (JP); Yanyan Liu, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 108 days.

(21) Appl. No.: 16/040,868

(22) Filed: Jul. 20, 2018

(65) Prior Publication Data

US 2018/0356330 A1   Dec. 13, 2018

Related U.S. Application Data

(63) Continuation of application No. PCT/JP2017/001955, filed on Jan. 20, 2017.

(30) Foreign Application Priority Data

Jan. 29, 2016 (JP) .............................. JP2016-016018

(51) Int. Cl.
*G01N 15/14* (2006.01)
*G01N 15/00* (2006.01)
(Continued)

(52) U.S. Cl.
CPC ......... *G01N 15/1404* (2013.01); *G01N 15/00* (2013.01); *G01N 15/1459* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 4,939,925 A * | 7/1990 | Sakuma | G01N 33/491 |
| | | | 73/61.63 |
| 5,726,751 A | 3/1998 | Altendorf et al. | |

(Continued)

FOREIGN PATENT DOCUMENTS

| | | |
|---|---|---|
| CN | 1739018 A | 2/2006 |
| CN | 103025859 A | 4/2013 |

(Continued)

OTHER PUBLICATIONS

The extended European search report dated Sep. 5, 2019 in a counterpart European patent application No. 17744092.2.
(Continued)

*Primary Examiner* — Lindsay J Uhl
(74) *Attorney, Agent, or Firm* — Crowell & Moring LLP

(57) ABSTRACT

Provided is a biological sample imaging device and a biological sample imaging method that are capable of disposing a sufficient number of large-sized particles in a biological sample so as to be moderately dispersed within an imaging range. The biological sample imaging method includes: a first step of introducing a biological sample containing particles into a liquid flow channel; a second step of causing the biological sample introduced into the liquid flow channel to flow in a forward direction; a third step of causing the biological sample to flow in a reverse direction after the second step; and an imaging step of taking, in an imaging cell, images of the particles contained in the biological sample that remains in the liquid flow channel after the third step.

20 Claims, 11 Drawing Sheets

FORWARD DIRECTION

(51) Int. Cl.
  *G01N 33/493* (2006.01)
  *G01N 35/08* (2006.01)
  *G01N 15/04* (2006.01)
  *G01N 15/06* (2006.01)
  *H04N 5/225* (2006.01)

(52) U.S. Cl.
  CPC ........... *G01N 33/493* (2013.01); *G01N 35/08* (2013.01); *G01N 15/06* (2013.01); *G01N 2015/045* (2013.01); *G01N 2015/1409* (2013.01); *H04N 5/225* (2013.01)

(56) References Cited

U.S. PATENT DOCUMENTS

| | | | | |
|---|---|---|---|---|
| 6,251,615 | B1* | 6/2001 | Oberhardt | G01N 15/147 422/73 |
| 8,409,509 | B2* | 4/2013 | Srienc | G01N 15/1459 422/82.11 |
| 2002/0028471 | A1 | 3/2002 | Oberhardt | |
| 2007/0281311 | A1* | 12/2007 | Roth | G01N 33/54333 436/524 |
| 2008/0070311 | A1* | 3/2008 | Li | G01N 15/1459 436/63 |
| 2009/0206234 | A1 | 8/2009 | Okuda et al. | |
| 2012/0048734 | A1* | 3/2012 | Sugiyama | G01N 35/1095 204/453 |
| 2012/0134559 | A1* | 5/2012 | Suzuki | G01N 15/1404 382/128 |
| 2013/0274119 | A1 | 10/2013 | Knutson et al. | |
| 2014/0272965 | A1* | 9/2014 | Handique | B01L 7/00 435/6.12 |
| 2015/0000428 | A1* | 1/2015 | Fukuda | G01N 35/1009 73/864.11 |
| 2015/0209784 | A1 | 7/2015 | Hayden et al. | |
| 2018/0372719 | A1* | 12/2018 | Frischauf | G01N 33/4915 |

FOREIGN PATENT DOCUMENTS

| | | |
|---|---|---|
| CN | 104380080 A | 2/2015 |
| JP | 2015-010894 | 1/2015 |
| WO | 97/12223 A1 | 4/1997 |
| WO | 99/42809 A1 | 8/1999 |
| WO | WO 00/70385 | 11/2000 |
| WO | WO 2008/007725 | 1/2008 |
| WO | WO 2013/056415 | 4/2013 |

OTHER PUBLICATIONS

The Chinese Office Action dated Apr. 2, 2020 in a counterpart Chinese patent application No. 201780007712.8.
A Communication pursuant to Article 94(3) EPC dated Jun. 15, 2021 in a counterpart European patent application No. 17744092.2.
A Chinese Office Action dated Mar. 1, 2021 in a counterpart Chinese patent application No. 201780007712.8.

* cited by examiner

FORWARD DIRECTION

REVERSE DIRECTION

BIOLOGICAL SAMPLE IMAGING DEVICE AND BIOLOGICAL SAMPLE IMAGING METHOD

RELATED APPLICATIONS

This application is a continuation of International Application PCT/JP2017/001955 filed on Jan. 20, 2017, which claims benefit of Japanese patent application JP 2016-016018 filed on Jan. 29, 2016, both of which are incorporated herein by reference in their entireties.

BACKGROUND OF THE INVENTION

1. Field of the Invention

The present invention relates to a biological sample imaging device and a biological sample imaging method, and particularly to imaging of liquid biological samples containing particles, such as urine and blood.

2. Description of the Related Art

A urine sample contains particles such as red blood cells, white blood cells, epithelial cells, and urinary casts, and observing these particles in the urine sample is effective in diagnosing diseases of the kidney and the urinary tract. International Publication WO 2008/007725 and International Publication WO 2013/056415 each disclose a device for imaging particles contained in a biological sample such as a urine sample.

SUMMARY OF THE INVENTION

In a test for a liquid biological sample such as a urine sample, adopting a structure, in which the biological sample is supplied from a container to an imaging cell (imaging range) through a liquid flow channel such as a tube or a pipe, is advantageous for automation of the test. In the process of investigating this structure, the inventors of the present invention have obtained the findings below.

That is, when the biological sample is caused to flow through the liquid flow channel as described above, an axial concentration effect acts on the particles in the biological sample. That is, according to fluid dynamics, the flow rate of the biological sample increases as the biological sample approaches the center axis of the liquid flow channel, and the particles in the biological sample gather around the center axis of the liquid flow channel, where the flow rate is highest. This axial concentration effect greatly acts on large-sized particles. As a result, the large-sized particles are flowed at a high flow rate to the downstream side, and the density of the large-sized particles increases near a downstream end of the biological sample (at the head of the biological sample) flowing through the liquid flow channel. In a urine sample, generally, large-sized particles such as epithelial cells and urinary casts are low in density, but the density of these particles can be increased in a downstream end portion of the biological sample by using the aforementioned axial concentration effect. By increasing the density of the particles, the particles can be efficiently reflected in images. Meanwhile, in image-taking with a camera, an imaging range has a two-dimensional expansion to some extent. However, if a particle imaging range is set in the downstream end portion of the biological sample, large-sized particles are concentrated and overlap each other in a downstream end portion of the imaging range, which makes it difficult to reflect the individual particles in images. Furthermore, if the imaging range is set on the upstream side of the downstream end portion of the biological sample so as to be apart from the downstream end portion, there is a possibility that a sufficient number of large-sized particles are not present within the imaging range. In this case, a sufficient number of large-sized particles cannot be reflected in images.

Therefore, an object of the present invention is to provide a biological sample imaging device and a biological sample imaging method that are capable of disposing a sufficient number of large-sized particles in a biological sample so as to be moderately dispersed within an imaging range.

A biological sample imaging device according to one aspect of the present invention includes: a liquid flow channel through which a liquid biological sample containing particles flows, the liquid flow channel having, at a predetermined position, an imaging range within which images of the particles contained in the biological sample are taken; a pump configured to cause the biological sample, which has been introduced from a container into the liquid flow channel, to flow in a forward direction from an upstream side toward a downstream side or in a direction reverse to the forward direction; a pump controller configured to cause the pump to sequentially perform a first operation of causing the biological sample introduced into the liquid flow channel to flow in the forward direction, and a second operation of causing the biological sample to flow in the reverse direction; and an imaging unit configured to take, within the imaging range, images of the particles contained in the biological sample that remains in the liquid flow channel after the second operation.

A biological sample imaging method includes: a first step of introducing a biological sample containing particles into a liquid flow channel; a second step of causing the biological sample introduced into the liquid flow channel to flow in a forward direction from an upstream side toward a downstream side; a third step of causing the biological sample to flow in a reverse direction after the second step; and an imaging step of taking, within an imaging range set on the liquid flow channel, images of the particles contained in the biological sample that remains in the liquid flow channel after the third step.

According to the present invention, it is possible to realize a biological sample imaging device and a biological sample imaging method that are capable of disposing a sufficient number of large-sized particles in a biological sample so as to be moderately dispersed within an imaging range.

These and other objects, features, aspects and advantages of the present invention will become more apparent from the following detailed description of the present invention when taken in conjunction with the accompanying drawings.

DETAILED DESCRIPTION OF THE PREFERRED EMBODIMENTS

Hereinafter, an embodiment of the present invention will be described in detail with reference to the drawings.

Figure 1:
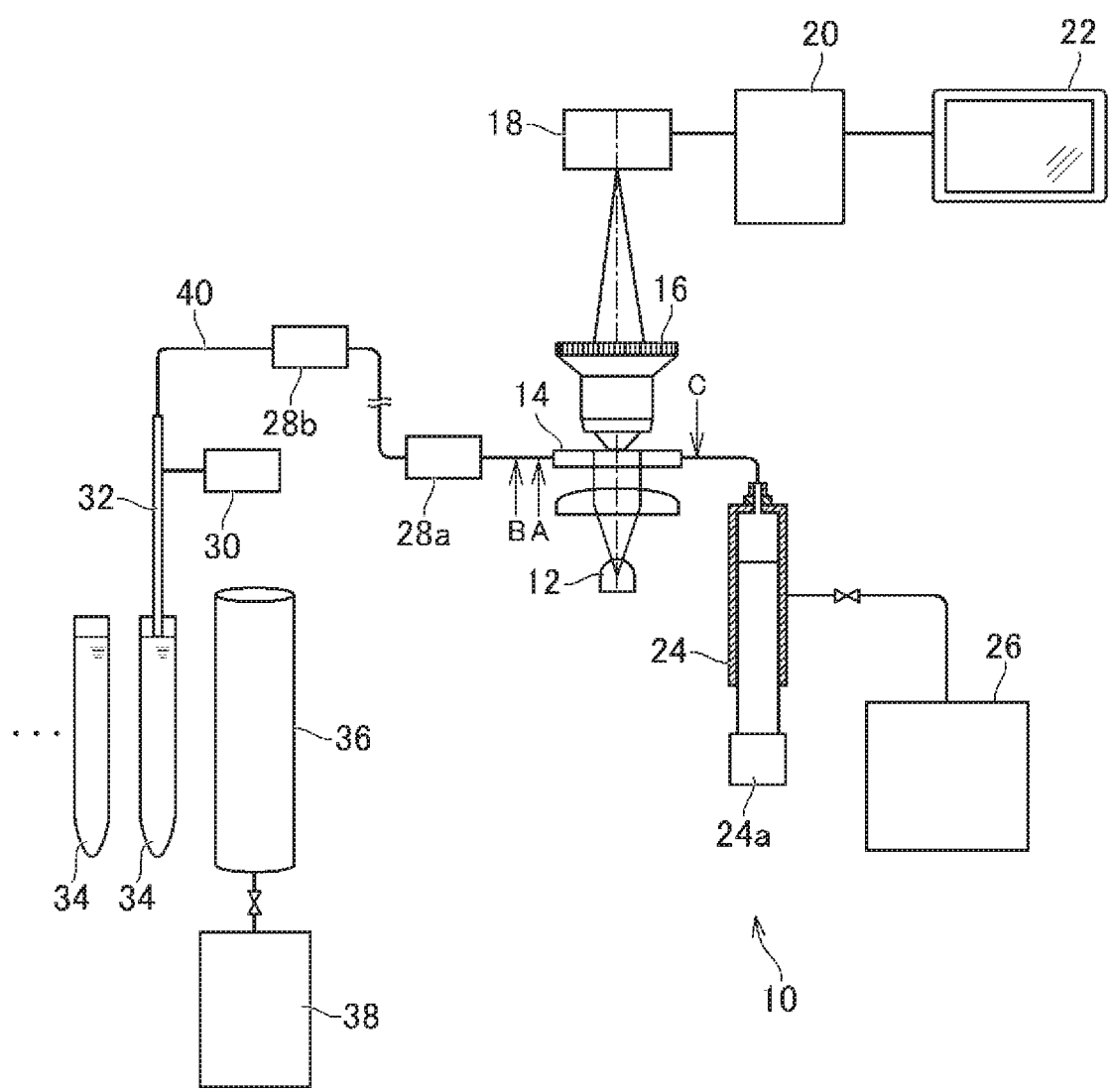
FIG. 1 is a is a configuration diagram of a biological sample imaging device according to one embodiment of the present invention.

FIG. 1 is a configuration diagram showing a biological sample imaging device according to an embodiment of the present invention. The biological sample imaging device 10 shown in FIG. 1 is an apparatus for taking images of particles in a liquid biological sample containing the particles. In this embodiment, a urine sample is used as an example of the biological sample, and images of particles such as red blood cells, white blood cells, epithelial cells, and urinary casts in the urine sample are taken by the biological sample imaging device 10. Examples of the epithelial cells include squamous cells, transitional cells, and tubular epithelial cells. Examples of the urinary casts include hyaline casts, epithelial casts, red blood cell casts, white blood cell casts, fatty casts, granular casts, and waxy casts.

The biological sample is not limited to urine, and may be blood, coelomic fluid, or the like. The biological sample may be a liquid directly collected from an organism, or may be a sample obtained by diluting the liquid with another liquid. Alternatively, the biological sample may be a sample obtained by dissolving particles collected from an organism into a liquid.

Of the particles contained in the urine sample, particles such as red blood cells and white blood cells, each having a particle size of about 7 μm, are referred to as small particles in the present embodiment. Meanwhile, particles such as epithelial cells and urinary casts, each having a particle size of about 20 to 40 μm, are referred to as large particles in the present embodiment.

As shown in FIG. 1, the biological sample imaging device 10 according to the present embodiment includes a liquid flow channel 40, a light source 12, an objective lens 16, a camera 18, a data processing unit 20, a display unit 22, a syringe pump 24, a washing liquid container 26, a suction nozzle actuator 30, a washing chamber 36, and a waste liquid container 38. The liquid flow channel 40 includes a rod-shaped hollow suction nozzle 32, a liquid flow channel inside a second sensor 28b, a liquid flow channel inside a first sensor 28a, and an imaging cell 14 arranged in order from the upstream side. The liquid flow channel 40 further includes tubes 41, such as silicon tubes, connected to these components. The imaging cell 14 is formed from a translucent material into a plate shape. The imaging cell 14 has an inner space formed in a flat rectangular-parallelepiped shape, through which the urine sample flows. Thus, the imaging cell 14 allows observation of the urine sample held in the inner space from the outside. An upstream end of the liquid flow channel 40 is a tip of the suction nozzle 32, and a downstream end thereof is a suction/discharge port of the syringe pump 24. An inner space of the liquid flow channel 40 has a circular cross section, except a portion inside the imaging cell 14. On the liquid flow channel 40, a first position A is set on the upstream side of the imaging cell 14, and a second position B is set on the upstream side of the first position A. The first position A and the second position B will be described later in detail.

The light source 12 includes a convex lens and a light emitting element such as an LED. The light source 12 is disposed directly below the imaging cell 14. Light emitted from the light emitting element is converted to parallel light by the convex lens, and the parallel light enters the imaging cell 14 made of a translucent material, from a lower portion of the imaging cell 14. The camera 18 is a CCD image sensor or a CMOS image sensor. The camera 18 is disposed directly above the imaging cell 14 together with the objective lens 16. The objective lens 16 and the camera 18 constitute a microscope camera. The microscope camera generates image data of the urine sample filled in the imaging cell 14. The display unit 22 is a display panel such as an LCD or an OLED. The display unit 22 displays information such as the image data generated by the camera 18.

The data processing unit 20 is a computer system composed of a CPU and a memory as main components, and the camera 18 and the display unit 22 are connected to the data processing unit 20. Furthermore, although not illustrated in FIG. 1, the following components are also connected to the data processing unit 20: the light source 12; a piston actuator 24a of the syringe pump 24; a solenoid valve provided in the tube between the syringe pump 24 and the washing liquid container 26; the first sensor 28a; the second sensor 28b; the suction nozzle actuator 30; and a solenoid valve provided in a drain tube of the washing chamber 36. An image analysis program and various control programs are installed on the data processing unit 20. The data processing unit 20 causes the display unit 22 to display the image data generated by the camera 18. In addition, the data processing unit 20 analyzes the image data generated by the camera 18, and detects particles reflected in the image data. Moreover, the data processing unit 20 controls the piston actuator 24a, the suction nozzle actuator 30, and the respective solenoid valves. Of the various functions to be implemented by the data processing unit 20, part or all of them may be implemented by another type of hardware such as ASIC or FPGA.

The syringe pump 24 generates a negative pressure or a positive pressure with respect to the liquid flow channel 40 to cause a liquid or a gas to flow through the liquid flow channel 40 in a forward direction from the upstream end toward the downstream end or in a direction reverse to the forward direction. Specifically, the syringe pump 24 sucks the urine sample from a sample container 34 such as a test tube, and fills the inner space of the imaging cell 14 with the urine sample. Further, the syringe pump 24 causes a liquid or a gas in the liquid flow channel 40 to flow reversely. The syringe pump 24 includes a cylinder and a piston that is inserted in the cylinder, and the piston actuator 24a is mounted to the piston. In accordance with a command from the data processing unit 20, the piston actuator 24a, which is an electric drive means such as a motor, pulls out the piston from the cylinder (forward actuation), or pushes the piston into the cylinder (reverse actuation). An opening is provided at a side surface of the cylinder. A tube, which connects the inside of the washing liquid container 26 to the inside of the syringe pump 24, is connected to the opening. When the piston is pulled out from the cylinder and thereby the inner space between the piston and the cylinder comes to have a predetermined capacity or more, the inside of the washing liquid container 26 becomes communicable with the inside of the syringe pump 24.

The suction nozzle actuator 30 causes the suction nozzle 32 to move in the up-down and left-right directions in accordance with a command from the data processing unit 20. Specifically, a plurality of sample containers 34 held in a rack are transported, by a transporting means such as a belt conveyor, to a suction position of the biological sample imaging device 10. The suction nozzle actuator 30 inserts the suction nozzle 32 in one of the sample containers 34 sequentially selected by the data processing unit 20, and pulls out the suction nozzle 32 from the sample container 34. When the suction nozzle 32 or the liquid flow channel 40 is washed, the suction nozzle actuator 30 inserts the suction nozzle 32 in the washing chamber 36.

Each of the first sensor 28a and the second sensor 28b outputs data according to the type of an object (liquid or gas) that flows through a sensor position in the liquid flow channel 40. For example, a conductivity sensor may be used as the first sensor 28a and the second sensor 28b. The conductivity sensor is provided so as to come into contact with the biological sample that passes through the liquid flow channel 40. For example, the conductivity sensor includes two tubular electrodes separately disposed on the upstream side and the downstream side. The conductivity sensor outputs the conductivity of the object that flows between the electrodes. Instead of the conductivity sensor, an optical sensor may be used as the first sensor 28a and the second sensor 28b. The optical sensor includes a light emitter and a light receiver arranged opposed to each other via a tube in which the biological sample flows. An object that flows in the tube is irradiated with light emitted from the light emitter, and a signal reflecting the intensity of the light that has transmitted through the object is outputted from the light receiver.

Figure 2A:
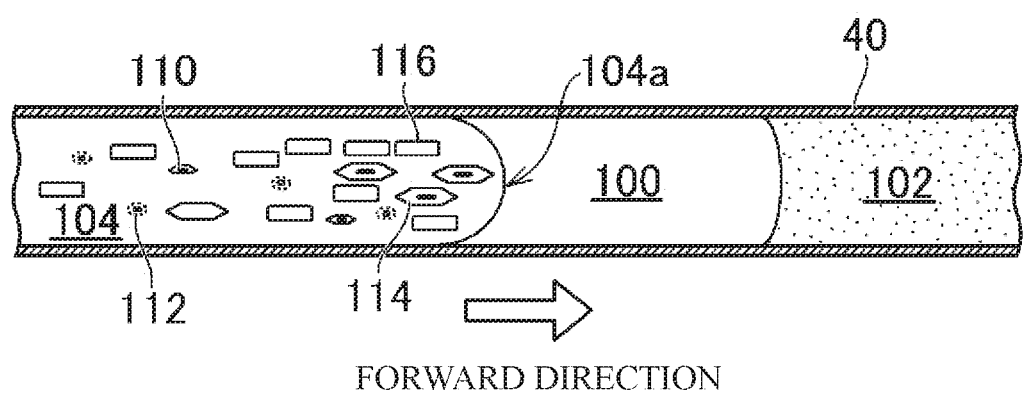
FIG. 2A is a diagram schematically showing the inside of a liquid flow channel when a pump is forwardly actuated.

A description is now given of how particles in the biological sample behave when the biological sample flows in the liquid flow channel 40. FIG. 2A schematically shows the inside of a tube 41 during the forward actuation of the syringe pump 24.

As described later in detail, the liquid flow channel 40 such as the tube 41 is filled with a washing liquid 102 in the initial state. When a biological sample 104 is filled in the imaging cell 14, firstly, a small amount of air 100 is sucked, and thereafter, a predetermined amount of the biological sample 104 is sucked from the sample container 34. Therefore, as shown in FIG. 2A, the air 100 (air gap) is positioned on the upstream side of the washing liquid 102, and the biological sample 104 is positioned on the upstream side of the air 100.

As already described above, in the liquid flow channel 40 such as the tube 41, the flow rate of the biological sample increases as the biological sample approaches the center axis of the liquid flow channel 40. Then, the particles in the biological sample gather around the center axis of the liquid flow channel 40, where the flow rate is highest. This axial concentration effect greatly acts on large particles such as epithelial cells 114 and urinary casts 116. As a result, the epithelial cells 114 and the urinary casts 116 are carried to the downstream side at a high flow rate. Thus, as shown in FIG. 2A, the density of the epithelial cells 114 and the urinary casts 116 is increased around a downstream end 104a of the biological sample 104 which flows through the liquid flow channel 40. Since red blood cells 112 and white blood cells 110 have sufficiently small particle sizes with respect to the flow-rate profile of the liquid flow channel 40, the axial concentration effect can be ignored.

Figure 3:
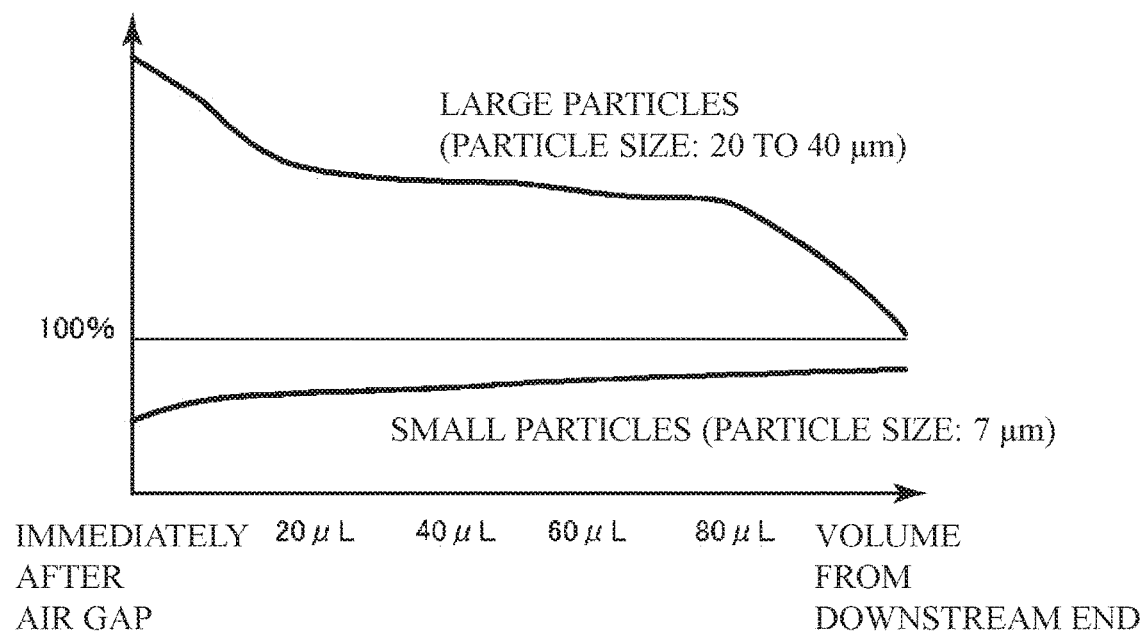
FIG. 3 is a distribution chart of large particles and small particles in a biological sample immediately after the pump is forwardly actuated.

FIG. 3 is a distribution chart of large particles and small particles in the biological sample 104 immediately after the syringe pump 24 is forwardly actuated. The vertical axis indicates a value obtained by dividing the particle density (number of particles per unit volume) in the liquid flow channel 40 by the particle density in the sample container 34. The horizontal axis indicates the volume from the downstream end 104a of the biological sample 104. As shown in FIG. 3, in the direction from the upstream end to the downstream end of the biological sample 104 (in the direction to the right in FIG. 3), the particle density of the large particles such as the epithelial cells 114 and the urinary casts 116 increases. That is, the particle density ratio of the large particles reaches about 300% near the downstream end 104a of the biological sample 104. That is, by causing the biological sample 104 to flow through the liquid flow channel 40, the effect of condensing the large particles can be obtained. Therefore, by taking images of an area around the downstream end 104a of the biological sample 104 after the biological sample 104 is caused to flow through the liquid flow channel 40, images of the large particles such as the epithelial cells 114 and the urinary casts 116 can be efficiently taken.

Unlike the large particles, the particle density ratio of the small particles such as the red blood cells 112 and the white blood cells 110 decreases in the direction from the upstream end to the downstream end of the biological sample 104. The particle density ratio of the small particles is less than 100% at any position. The reason of this is considered as follows. That is, as described above, the axial concentration effect hardly acts on the small particles. In addition, the biological sample 104 is diluted toward the downstream side by the washing liquid 102 attached to an inner wall surface of the liquid flow channel 40.

As described above, when the biological sample 104 is caused to flow through the liquid flow channel 40, the density of the large particles such as the epithelial cells 114 and the urinary casts 116 can be increased near the downstream end 104a of the biological sample 104. Increasing the density of the particles allows the particles to be efficiently reflected in images. However, as described later in detail, the imaging cell 14 has an inner space that expands in the horizontal direction, and the entirety or a part of the inner space is set as an imaging range for the camera 18. If the downstream end 104a of the biological sample 104 is located within the imaging range, the large particles are concentrated in a part of the imaging range, and are overlapped with each other in the vertical direction, which makes it difficult to reflect the individual particles in images. On the other hand, if a portion, of the biological sample 104, a predetermined distance apart from the downstream end 104a is located within the imaging range, there is a possibility that a sufficient number of large particles are not present in such a portion. In this case, a sufficient number of large particles cannot be reflected in images.

Therefore, in the present embodiment, a pump control is executed, by which the large particles concentrated around the downstream end 104a of the biological sample 104 is dispersed again. That is, in the present embodiment, forward actuation of the syringe pump 24 is temporarily stopped immediately before the biological sample 104 enters the inner space of the imaging cell 14. Specifically, when the downstream end 104a of the biological sample 104 has reached the first position A (refer to FIG. 1) that is set on the upstream side of the imaging cell 14, the operation of the syringe pump 24 is stopped. Then, the syringe pump 24 is reversely actuated until the downstream end 104a of the biological sample 104 reaches the second position B. The second position B is set on the upstream side relative to the first position A. That is, the biological sample 104 is pushed back to the upstream side.

Figure 2B:
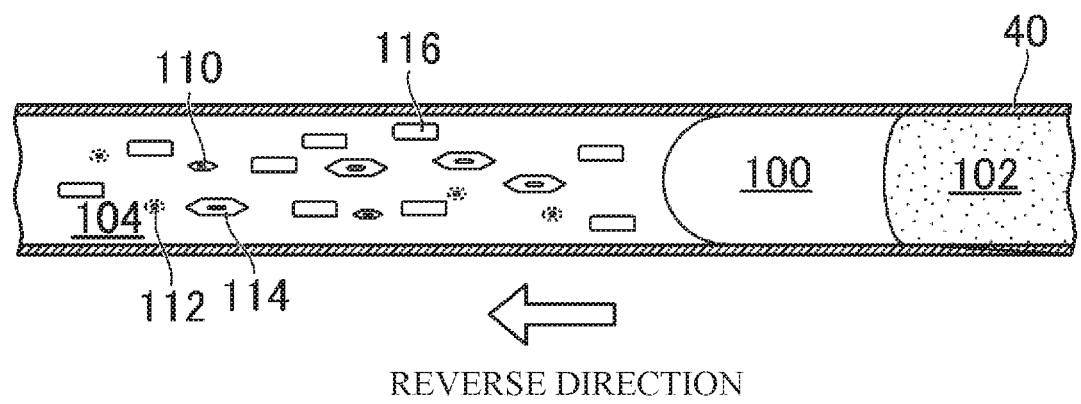
FIG. 2B is a diagram schematically showing the inside of the liquid flow channel when the pump is reversely actuated.

FIG. 2B schematically shows the inside of the liquid flow channel 40 during the reverse actuation of the syringe pump 24. When the syringe pump 24 is reversely actuated, the biological sample 104 moves to the upstream side, that is, toward the suction nozzle 32. Also in this case, the axial concentration effect greatly acts on the large particles such as the epithelial cells 114 and the urinary casts 116. Therefore, the large particles concentrated around the downstream end 104a move in the upstream direction relative to the small particles, as shown in FIG. 2B. Thus, by reversely actuating the syringe pump 24 only by a predetermined volume, the large particles concentrated around the downstream end 104a can be favorably dispersed to a portion apart from the downstream end 104a.

When the downstream end 104a of the biological sample 104 has reached the second position B, the syringe pump 24 is temporarily stopped, and then the syringe pump 24 is forwardly actuated until the downstream end 104a of the biological sample 104 reaches a third position C. The third position C is set on the downstream side of the imaging cell 14 in the liquid flow channel 40. Thus, the inner space of the imaging cell 14 can be filled with the biological sample 104.

Figure 4A:
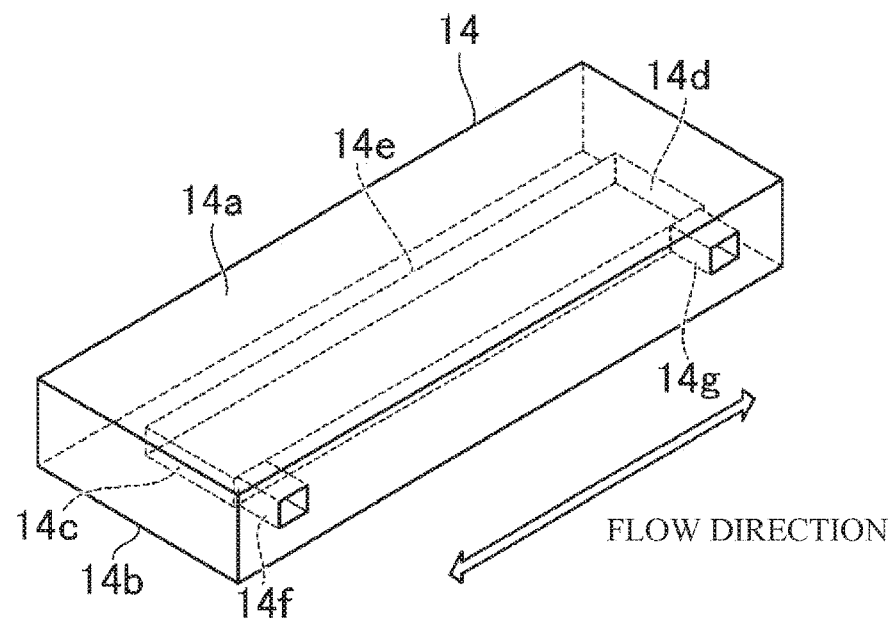
FIG. 4A is a perspective view showing an imaging cell.

A description is now given of the imaging cell 14. FIG. 4A is a perspective view of the imaging cell 14. As shown in FIG. 4A, the imaging cell 14 includes: an inner space 14e for holding a urine sample; and an inflow path 14f and an outflow path 14g, through which the inner space 14e communicates with the outside. The imaging cell 14 has a rectangular parallelepiped outer shape that is flat and extends in one direction. The inner space 14e also has a rectangular parallelepiped shape that is flat and extends in one direction. The inner space 14e is arranged along the outer shape of the imaging cell 14. The imaging cell 14 is placed so that the bottom surface of the inner space 14e becomes horizontal.

The inner space 14e is sandwiched, in the vertical direction, by a thin plate part 14a and a thin plate part 14b which are parallel and opposed to each other. At least the thin plate part 14a and the thin plate part 14b of the imaging cell 14 are formed from a translucent material such as glass or resin.

The inner space 14e has a rectangular parallelepiped shape that extends in one direction as described above, and the surface at one end thereof in the longitudinal direction is an upstream end 14c while the surface at the other end thereof in the longitudinal direction is a downstream end 14d. The inflow path 14f communicating with an opening at a side surface of the imaging cell 14 is formed in a portion, of a side wall of the imaging cell 14, right next to the upstream end 14c of the inner space 14e. Likewise, the outflow path 14g communicating with an opening at the side surface of the imaging cell 14 is formed in a portion, of the side wall of the imaging cell 14, right next to the downstream end 14d of the inner space 14e. A tube 41 communicating with the first sensor 28a is connected to the inflow path 14f, and a tube 41 communicating with the syringe pump 24 is connected to the outflow path 14g.

The light source 12 is disposed below the imaging cell 14, and parallel light enters the imaging cell 14 from the thin plate part 14b side. The microscope camera composed of the objective lens 16 and the camera 18 is disposed above the imaging cell 14. The microscope camera takes an image of the urine sample filled in the inner space 14e, through the thin plate part 14a. Although it is preferable that the imaging range (range utilized for display and/or image analysis) of the microscope camera is the entirety of the rectangular parallelepiped inner space 14e, the imaging range may be a part of the inner space 14e.

Figure 4B:
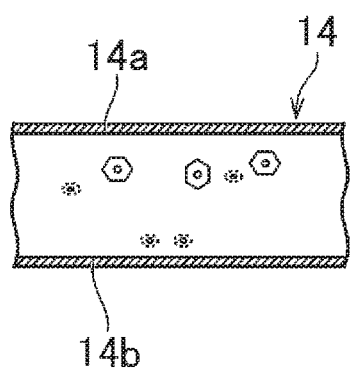
FIG. 4B is a diagram schematically showing a cross section of the imaging cell immediately after the imaging cell is filled with the biological sample.
Figure 4C:
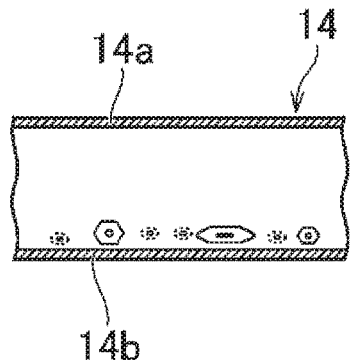
FIG. 4C is a diagram schematically showing a cross section of the imaging cell after a predetermined time period has passed from the filling of the imaging cell with the biological sample.

FIG. 4B schematically shows a cross section of the imaging cell 14 immediately after the imaging cell 14 has been filled with the biological sample 104. FIG. 4C schematically shows a cross section of the imaging cell 14 after a predetermined time period has passed from the filling with the biological sample 104. As shown in FIG. 4B, immediately after the imaging cell 14 has been filled with the biological sample 104, the particles are floating in the space between the thin plate part 14a and the thin plate part 14b. However, after the predetermined time period has passed, the particles are precipitated at the bottom as shown in FIG. 4C. The microscope camera composed of the objective lens 16 and the camera 18 is focused on the vicinity of the surfaces of the particles precipitated at the bottom, and takes a macrophotograph. According to the present embodiment, a sufficient number of large particles are present between the thin plate part 14a and the thin plate part 14b, and moreover, the large particles are favorably dispersed. Therefore, even when the large particles are precipitated at the bottom, the large particles hardly overlap each other in the vertical direction. As a result, images of the individual large particles can be clearly taken.

Although the width of the inner space 14e is sufficiently large, the height of the inner space 14e, i.e., the interval between the thin plate part 14a and the thin plate part 14b, is smaller than the dimension of any part of the liquid flow channel 40, except the imaging cell 14. In particular, the height of the inner space 14e is smaller than the inner diameters of the suction nozzle 32 and the tube 41 provided on the upstream side relative to the imaging cell 14. By adopting this configuration, the particles in the inner space 14e can be quickly precipitated to be ready for image-taking.

Figure 5:
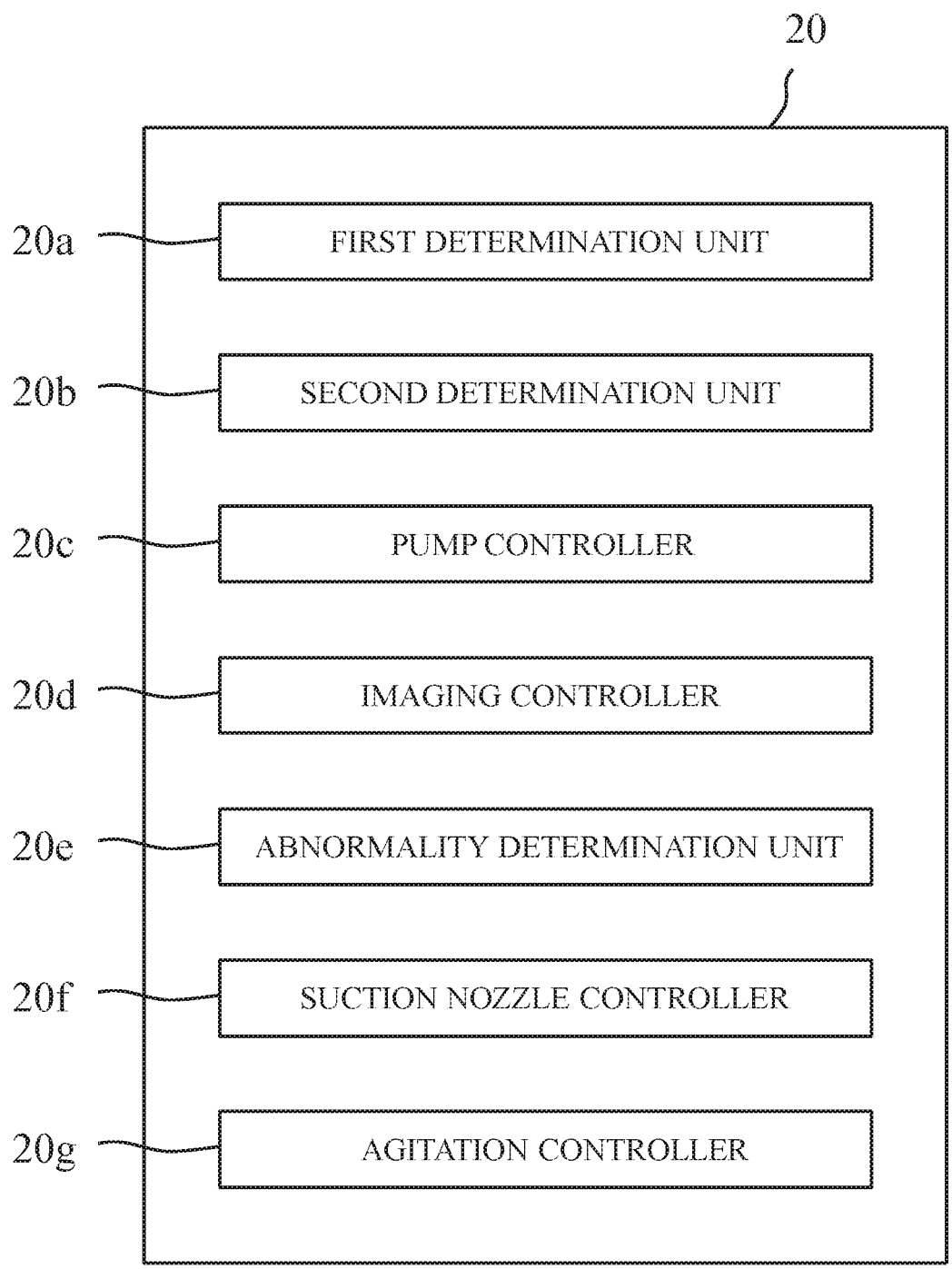
FIG. 5 is a functional block diagram of a data processing unit.

FIG. 5 is a functional block diagram showing the data processing unit 20. As described above, the data processing unit 20 is configured by a computer system, and implements various functions by executing programs. As shown in FIG. 5, the data processing unit 20 functionally includes a first determination unit 20a, a second determination unit 20b, a pump controller 20c, an imaging controller 20d, an abnormality determination unit 20e, a suction nozzle controller 20f, and an agitation controller 20g.

The first determination unit 20a determines that the downstream end 104a of the biological sample 104 has reached the first position A provided on the liquid flow channel 40. For example, the first determination unit 20a may determine that the downstream end 104a of the biological sample 104 has reached the first position A, on the basis of the suction amount or the discharge amount of the syringe pump 24. The suction amount or the discharge amount of the syringe pump 24 can be determined based on the operation amount of the piston actuator 24a. In addition, the cross-sectional area of the liquid flow channel 40 is already known, and the internal capacity of the liquid flow channel 40 from the upstream end to the first position A is also already known. Accordingly, when the suction amount of the syringe pump 24 has reached the known internal capacity, the first determination unit 20a can determine that the downstream end 104a of the biological sample 104 has reached the first position A provided on the liquid flow channel 40.

The first determination unit 20a may determine that the downstream end 104a of the biological sample 104 has reached the first position A, on the basis of an output from a sensor provided in the liquid flow channel 40. For example, a conductivity sensor may be disposed at the first position A, and the first determination unit 20a may determine that the downstream end 104a of the biological sample 104 has reached the first position A, on the basis of the conductivity outputted from the conductivity sensor. According to the present embodiment, since the air 100 is caused to be adjacent to the downstream side of the biological sample 104, when the conductivity of the biological sample 104 is detected while the conductivity of the air 100 is being detected, this timing allows the determination that the downstream end 104a of the biological sample 104 has reached the position of the conductivity sensor, i.e., the first position A.

Alternatively, the first determination unit 20a may determine that the downstream end 104a of the biological sample 104 has reached the first position A, on the basis of both an output from the sensor and the suction amount/discharge amount of the syringe pump 24. For example, the first sensor 28a is mounted on the upstream side relative to the first position A, and the internal capacity of the liquid flow channel 40 from the detection position of the first sensor 28a to the first position A is already known. Therefore, when the suction amount of the syringe pump 24 reaches the known internal capacity after the timing when the first sensor 28a determines that the downstream end 104a of the biological sample 104 has reached the detection position of the first sensor 28a, the first determination unit 20a can determine that the downstream end 104a of the biological sample 104 has reached the first position A.

The second determination unit 20b determines that the downstream end 104a of the biological sample 104 has reached the second position B provided on the liquid flow channel 40. This determination can be performed similarly to the determination by the first determination unit 20a. For example, the internal capacity of the liquid flow channel 40 from the first position A to the second position B is already known. Therefore, the syringe pump 24 is reversely actuated from the state where the downstream end 104a of the biological sample 104 is located at the first position A, then if the discharge amount thereof reaches the known internal capacity, it can be determined that the downstream end 104a has reached the second position B.

Alternatively, the second determination unit 20b may determine that the downstream end 104a of the biological sample 104 has reached the second position B, on the basis of an output from a sensor provided in the liquid flow channel 40. For example, a conductivity sensor may be disposed at the second position B, and the second determination unit 20b may determine that the downstream end 104a of the biological sample 104 has reached the second position B, on the basis of the conductivity outputted from the conductivity sensor. According to the present embodiment, since the air 100 is caused to be adjacent to the downstream side of the biological sample 104, when the conductivity of the air 100 is detected while the conductivity of the biological sample 104 is being detected, this timing allows the determination that the downstream end 104a of the biological sample 104 has reached the position of the conductivity sensor, i.e., the second position B.

The pump controller 20c instructs the operation of the piston actuator 24a. In particular, when the biological sample 104 is filled in the imaging cell 14, the pump controller 20c causes the syringe pump 24 to sequentially perform: a first operation (forward actuation) in which the biological sample 104, having been introduced into the liquid flow channel 40, is caused to flow in the forward direction, and the downstream end 104a thereof is caused to reach the first position A; and a second operation (reverse operation) in which the biological sample 104 is caused to flow in the reverse direction, and the downstream end 104a thereof is caused to reach the second position B. The first operation includes: a liquid introducing operation of introducing a predetermined amount of the biological sample 104 from the tip of the suction nozzle 32 into the liquid flow channel 40; and an air introducing operation of, after the liquid introducing operation, pulling up the suction nozzle 32 from the sample container 34, and introducing air from the tip of the suction nozzle 32 into the liquid flow channel 40. Thus, by causing air to flow through the upstream side of the biological sample 104, the amount of the biological sample 104 required for image-taking can be reduced. After the second operation, the pump controller 20c causes the piston actuator 24a to perform a third operation of causing the biological sample 104 to flow in the forward direction again. Thus, the downstream end 104a of the biological sample 104 is caused to reach the third position C. The third position C may be set at the downstream end 14d of the inner space 14e of the imaging cell 14, or at any position that is near the imaging cell 14 and on the downstream side relative to the downstream end 14d. The third operation is performed with the tip of the suction nozzle 32 being pulled up from the liquid surface in the sample container 34.

If the third position C is set on the downstream side relative to the inner space 14e of the imaging cell 14, the downstream end 104a of the biological sample 104 can be prevented from entering the imaging range. There is a possibility that the washing liquid 102 or the like attached to the inner wall of the liquid flow channel 40 is mixed into a portion around the downstream end 104a of the biological sample 104. If the third position C is set on the downstream side relative to the inner space 14e of the imaging cell 14, image-taking of the biological sample 104 can be performed while avoiding such a portion.

Since the aforementioned second operation is performed in the present embodiment, the large particles concentrated around the downstream end 104a of the biological sample 104 due to the first operation are pushed back to the upstream side, whereby a sufficient number of large particles can be ensured within the imaging range. Further, the second operation allows the large particles to be favorably dispersed within the imaging range.

The first position A is set on the upstream side relative to the inner space 14e of the imaging cell 14, which is the imaging range. Thus, the large particles can be dispersed in the liquid flow channel 40 at the upstream side of the imaging cell 14, and thereafter, the biological sample 104 can be filled in the imaging cell 14. Therefore, the large particles such as the epithelial cells 114 and the urinary casts 116 can be prevented from clogging the imaging cell 14. That is, since the height of the inner space 14e of the imaging cell 14 is very low as mentioned above, clogging of the large particles is a concern. However, according to the present embodiment, such clogging can be prevented.

The internal capacity from the second position B to the tip of the suction nozzle 32 is desired to be greater than the internal capacity of the liquid flow channel 40 at least within the imaging range (the internal capacity of the inner space 14e of the imaging cell 14). Otherwise, the already sucked biological sample 104 is discharged from the tip of the suction nozzle 32 due to the second operation.

The internal capacity of the liquid flow channel 40 from the second position B to the upstream end 14c of the imaging cell 14 is desired to be not greater than 10 times the internal capacity of the liquid flow channel 40 within the imaging range, that is, the internal capacity of the inner space 14e of the imaging cell 14. Thus, the movement amount of the biological sample 104 during the third operation can be reduced, thereby preventing the large particles from being again concentrated around the downstream end 104a of the biological sample 104 due to the third operation.

The second operation is performed with the tip of the suction nozzle 32 being pulled up from the liquid surface in the sample container 34. Thus, air is prevented from being supplied into the sample container 34.

The internal capacity of the liquid flow channel 40 from the first position A to the second position B is desired to be not greater than one-tenth of the internal capacity from the tip of the suction nozzle 32 to the first position A. When the extent of pushing back the large particles in the reverse direction is relatively reduced, the particle condensing effect due to the axial concentration effect is maintained, whereby a sufficient number of large particles can be ensured within the imaging range.

When the operation of the syringe pump 24 is stopped after the third operation by the pump controller 20c, the imaging controller 20d waits for elapse of a predetermined time period required for precipitation of the particles, and then causes the camera 18 to take images of the particles in the biological sample 104 within the imaging range, that is, within the inner space 14e of the imaging cell 14. Thus, the images taken of the biological sample 104 are displayed on the display unit 22, or used for image analysis.

The imaging controller 20d takes images of the biological sample 104 for each of the plurality of sample containers 34 held in the rack. At this time, the pump controller 20c performs the aforementioned first to third operations for each biological sample 104.

The abnormality determination unit 20e detects an abnormality that the amount of the biological sample 104 sucked from the sample container 34 is less than a specified amount, when the biological sample 104 is supplied into the imaging cell 14. Specifically, a shortage monitoring period is provided after start of the air introduction in the first operation, and if air is detected by the second sensor 28b during the shortage monitoring period, it is determined that the biological sample 104 is insufficient. The shortage monitoring period is a period during which a specified amount of the biological sample 104 should pass through the detection position of the second sensor 28b. When such an abnormality is detected, the abnormality is displayed on the display unit 22, for example. The abnormality determination unit 20e can improve the reliability of the images of the biological sample 104. The suction nozzle controller 20f instructs the operation of the suction nozzle actuator 30.

Before the first operation by the pump controller 20c, the agitation controller 20g causes the biological sample 104 in the sample container 34 to be agitated. For example, an agitation nozzle (not shown) is inserted in the sample container 34, and a certain amount of the biological sample 104 is sucked by using an agitation pump (not shown), and thereafter, the sucked biological sample 104 is returned to the sample container 34 by the agitation pump, thereby agitating the biological sample 104 in the sample container 34. Alternatively, the biological sample 104 in the sample container 34 may be agitated by discharging air from the agitation nozzle. The biological sample 104 may be agitated by using the syringe pump 24 and the suction nozzle 32 in the same manner as described above. In the present embodiment, an exemplary structure is adopted in which an agitation nozzle (not shown) is formed integrally with the suction nozzle 32, and the biological sample 104 in the sample container 34 is agitated by using an agitation pump (not shown) different from the syringe pump 24. The integrated agitation nozzle and suction nozzle 32 can be actuated together by the suction nozzle actuator 30.

Figure 6A:
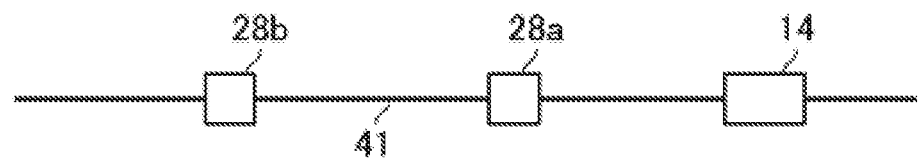
FIG. 6A is a diagram showing, in a time series manner, how an object such as a biological sample flows through the liquid flow channel.
Figure 6B:
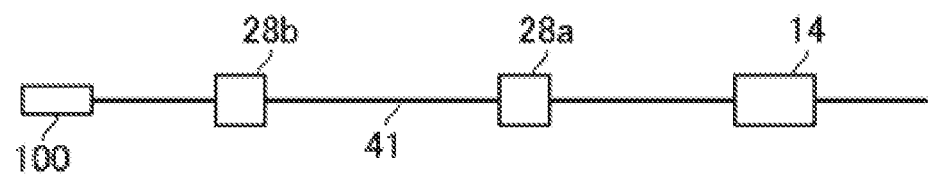
FIG. 6B is a diagram showing, in a time series manner, how an object such as a biological sample flows through the liquid flow channel.
Figure 6C:
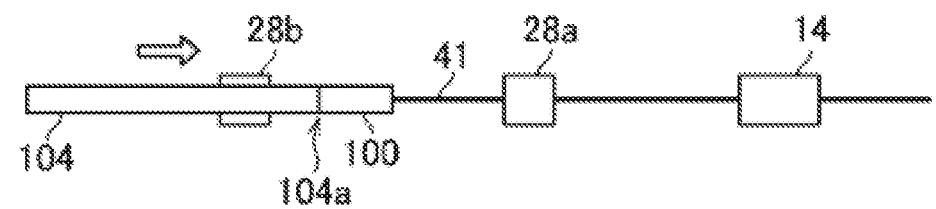
FIG. 6C is a diagram showing, in a time series manner, how an object such as a biological sample flows through the liquid flow channel.
Figure 6D:
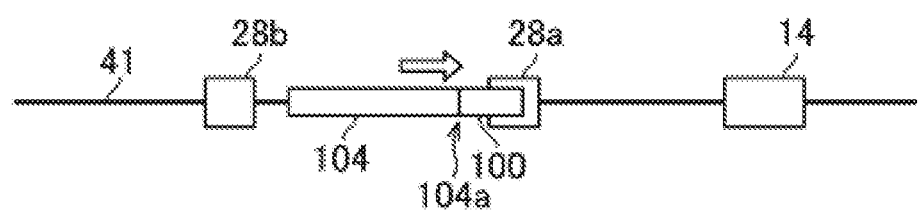
FIG. 6D is a diagram showing, in a time series manner, how an object such as a biological sample flows through the liquid flow channel.

Hereinafter, the operation of the biological sample imaging device 10 is described in a time series manner. FIGS. 6A to 6G show, in a time series manner, how the biological sample 104 flows through the liquid flow channel 40. FIG. 7A and FIG. 7B are flowcharts showing the operation of the biological sample imaging device 10.

When images of particles in a urine sample are taken by the biological sample imaging device 10, a plurality of sample containers 34 are transported to the suction position while being held in the rack as described above. The entirety of the liquid flow channel 40 is, in the initial state, filled with the washing liquid 102 (FIG. 6A). Next, the pump controller 20c causes the syringe pump 24 to suck a certain volume of air 100 while the suction nozzle 32 is not inserted in the sample container 34, thereby introducing the certain volume of air 100 to an end of the liquid flow channel 40 to form an air gap (S101 in FIG. 7A, and FIG. 6B). For example, about 25 μL of air 100 may be sucked into the liquid flow channel 40.

Next, the suction nozzle actuator 30 causes the suction nozzle 32 to be inserted in one sample container 34 together with an agitation nozzle (not shown) (S102 in FIG. 7A).

Then, the agitation controller 20g causes the biological sample 104 contained in the sample container 34 to be agitated (S103 in FIG. 7A).

Thereafter, the pump controller 20c forwardly drives the piston actuator 24a to suck a specified amount of the biological sample 104 from the sample container 34 (S104 in FIG. 7A). For example, about 300 μL of the biological sample 104 may be sucked into the liquid flow channel 40. During the suction process, the abnormality determination unit 20e monitors a rapid decrease in the conductivity outputted from the second sensor 28b, that is, it monitors passing of the air gap. If the conductivity does not rapidly decrease, the abnormality determination unit 20e determines that the operation of the syringe pump 24 is abnormal, and ends the process.

When suction of the specified amount of biological sample 104 is completed (FIG. 6C), the abnormality determination unit 20e determines whether or not the conductivity outputted from the second sensor 28b is equal to or higher than a predetermined threshold (S105 in FIG. 7A). If the conductivity is less than the predetermined threshold, the abnormality determination unit 20e determines that abnormality has occurred in the biological sample 104, and ends the process.

Thereafter, the suction nozzle controller 20f causes the suction nozzle actuator 30 to pull up the suction nozzle 32 from the sample container 34 (S106 in FIG. 7A). Next, the pump controller 20c causes air to be sucked from the suction nozzle 32 (S107 in FIG. 7A). In the initial stage of this suction process, a shortage monitoring period is set, and the abnormality determination unit 20e monitors a rapid decrease in the conductivity outputted from the second sensor 28b. If the conductivity rapidly decreases, the abnormality determination unit 20e determines that the biological sample 104 is less than the specified amount, and ends the process.

The pump controller 20c causes the suction of air to be performed until the air 100 is detected by the first sensor 28a (S108 in FIG. 7A). The suction of air causes the biological sample 104 having been introduced into the liquid flow channel 40 to move to the downstream side. If the conductivity that is outputted from the first sensor 28a rapidly decreases, it can be determined that the air 100 has taken the place of the object, i.e., the washing liquid 102, located at the detection position of the first sensor 28a. At this timing, the downstream end of the air 100 (air gap) reaches the detection position of the first sensor 28a (FIG. 6D).

Figure 6E:
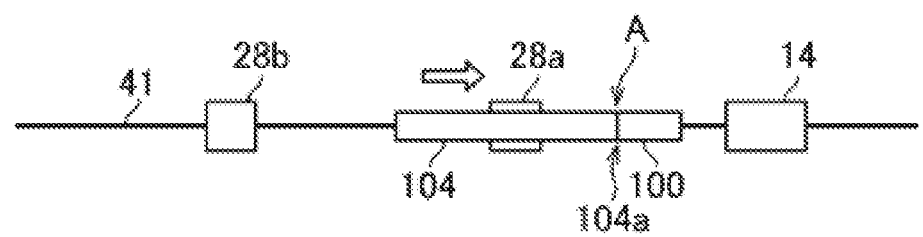
FIG. 6E is a diagram showing, in a time series manner, how an object such as a biological sample flows through the liquid flow channel.
Figure 7A:
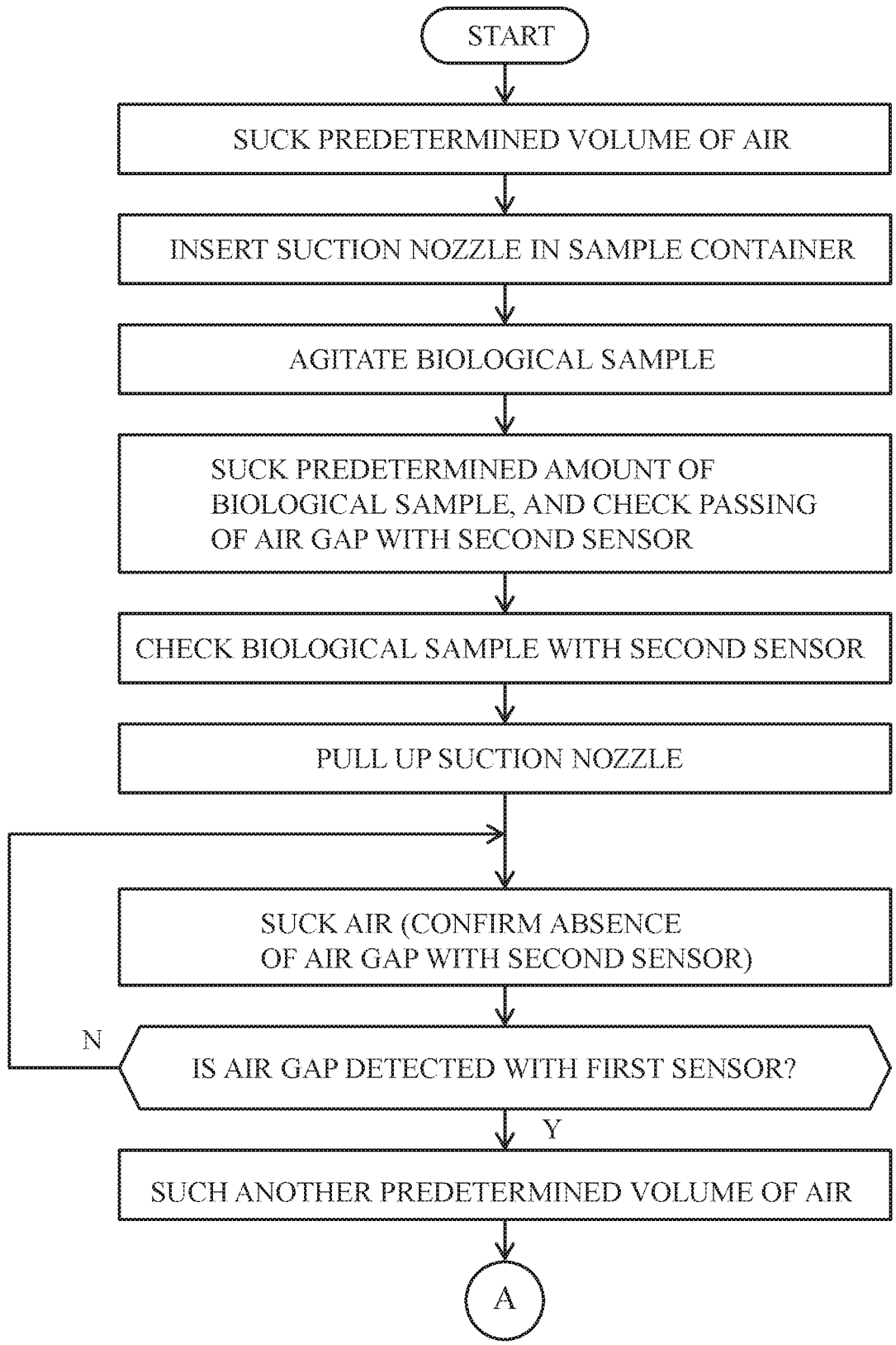
FIG. 7A is a flowchart showing the operation of the biological sample imaging device according to the embodiment of the present invention.
Figure 7B:
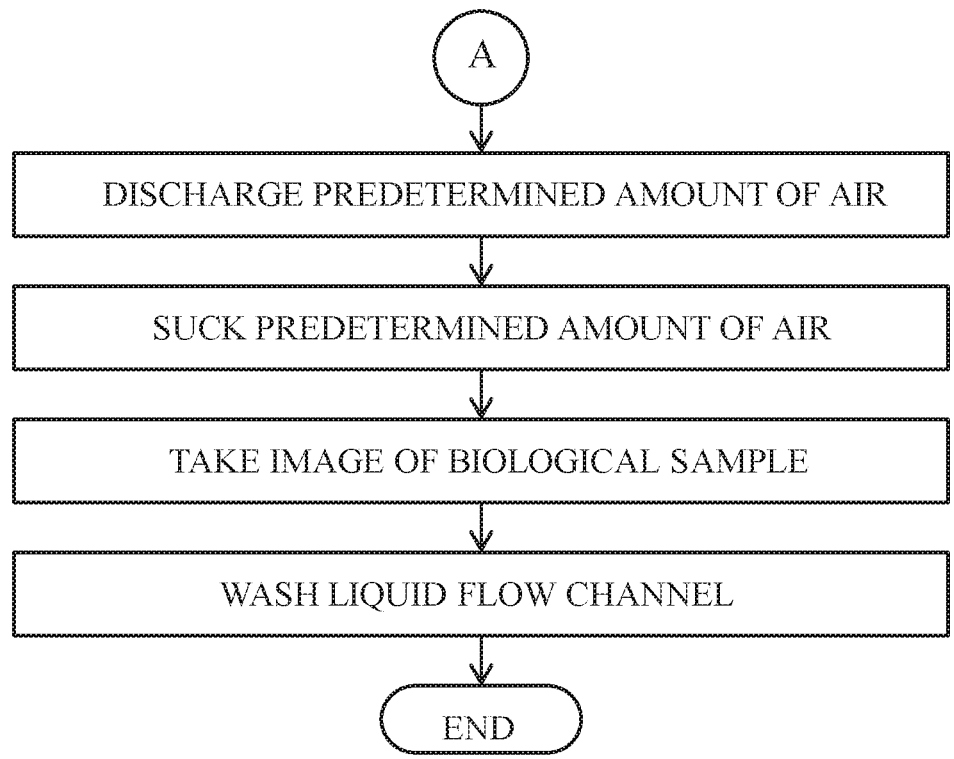
FIG. 7B is a flowchart showing the operation of the biological sample imaging device according to the embodiment of the present invention.

Thereafter, the pump controller 20c further causes a predetermined amount of air to be sucked (S109 in FIG. 7A, FIG. 6E). Specifically, the first determination unit 20a determines whether or not the suction amount of the syringe pump 24 has reached the predetermined amount, and the pump controller 20c stops the operation of the syringe pump 24 when the suction amount of the syringe pump 24 has reached the predetermined amount. The suction amount of the syringe pump 24 in S109 is a value obtained by adding the volume of the air 100 (air gap) to the internal capacity from the detection position of the first sensor 28a to the first position A. Thus, the downstream end 104a of the biological sample 104 reaches the first position A. The first position A may be provided about 60 μL upstream of the upstream end 14c of the inner space 14e of the imaging cell 14. The operation from S104 to S109 corresponds to the first operation of the syringe pump 24.

Figure 6F:
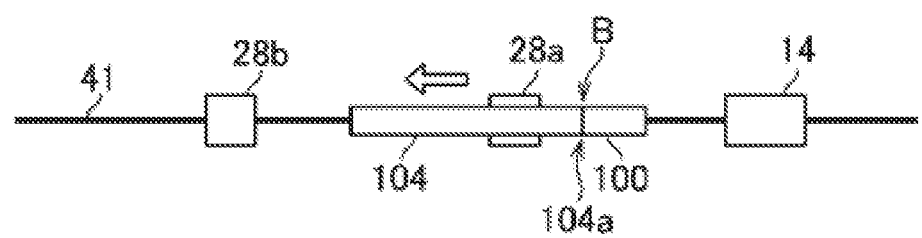
FIG. 6F is a diagram showing, in a time series manner, how an object such as a biological sample flows through the liquid flow channel.

Thereafter, the pump controller 20c instructs the piston actuator 24a to perform reverse actuation, thereby causing a predetermined amount of air to be discharged from the upstream end of the liquid flow channel 40 (S110 in FIG. 7B). Specifically, the second determination unit 20b determines whether or not the discharge amount of the syringe pump 24 has reached the predetermined amount, and the pump controller 20c stops the operation of the syringe pump 24 if the discharge amount of the syringe pump 24 has reached the predetermined amount. The discharge amount of the syringe pump 24 is equal to the internal capacity from the first position A to the second position B. For example, the discharge amount may be about 30 μL. Thus, the downstream end 104a of the biological sample 104 reaches the second position B (FIG. 6F). The operation in S110 corresponds to the second operation of the syringe pump 24.

Figure 6G:
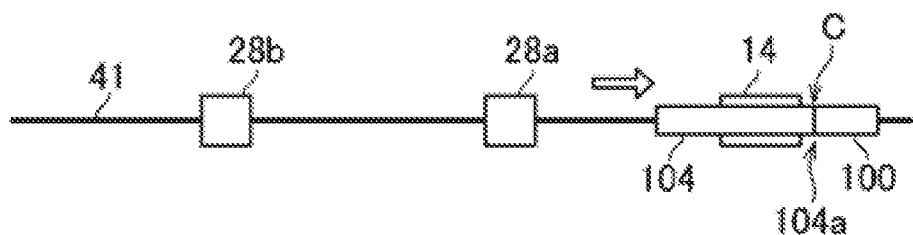
FIG. 6G is a diagram showing, in a time series manner, how an object such as a biological sample flows through the liquid flow channel.

Next, the pump controller 20c instructs the piston actuator 24a to perform forward actuation, and causes a predetermined amount of air to be sucked (S111 in FIG. 7B). Specifically, it is determined whether or not the suction amount of the syringe pump 24 has reached the predetermined amount, and the pump controller 20c stops the operation of the syringe pump 24 if the suction amount of the syringe pump 24 has reached the predetermined amount. The suction amount of the syringe pump 24 is equal to the internal capacity of the liquid flow channel 40 from the second position B to the third position C. For example, this suction amount may be about 120 μL. Thus, the downstream end 104a of the biological sample 104 reaches the third position C (FIG. 6G). For example, the capacity between the downstream end 14d of the imaging cell 14 and the third position C, which is the imaging range, may be 20 μL. In this case, if the capacity of the inner space 14e of the imaging cell 14 is 15 μL, a portion corresponding to 20 μL to 35 μL from the downstream end 104a of the biological sample 104 is filled in the inner space 14e of the imaging cell 14. The operation in S111 corresponds to the third operation of the syringe pump 24.

According to the aforementioned pump control, the biological sample 104 is filled in the inner space 14e of the imaging cell 14, and the imaging controller 20d causes image data of the biological sample 104 to be generated (S112 in FIG. 7B).

After the image-taking, washing of the liquid flow channel 40 and the syringe pump 24 is performed (S113 in FIG. 7B). Specifically, the suction nozzle controller 20f instructs the suction nozzle actuator 30 to insert the suction nozzle 32 in the washing chamber 36. At this timing, the piston of the syringe pump 24 is sufficiently pulled out, and the washing liquid stored in the washing liquid container 26 flows into the syringe pump 24 when the solenoid valve between the syringe pump 24 and the washing liquid container 26 is opened. The washing liquid immediately reaches the tip of the suction nozzle 32, whereby the inside of the liquid flow channel 40 and the inside of the syringe pump 24 are washed throughout. The air, the urine sample, and the washing liquid are discharged from the suction nozzle 32 to be stored in the waste liquid container 38. Thereafter, the solenoid valve provided in a drain of the washing chamber 36 is temporarily closed, whereby the washing liquid is stored in the washing chamber 36. Thereafter, the solenoid valve is opened. Thus, the outside of the suction nozzle 32 is also washed. The washing liquid may be supplied from the suction nozzle 32 or from an exclusive channel, to the washing chamber 36. When washing of the liquid flow channel 40 and the syringe pump 24 has ended, the suction nozzle 32 is pulled out from the washing chamber 36, and is moved to a stand-by position to ready for suction of the urine sample from the next sample container 34.

Figure 8A:
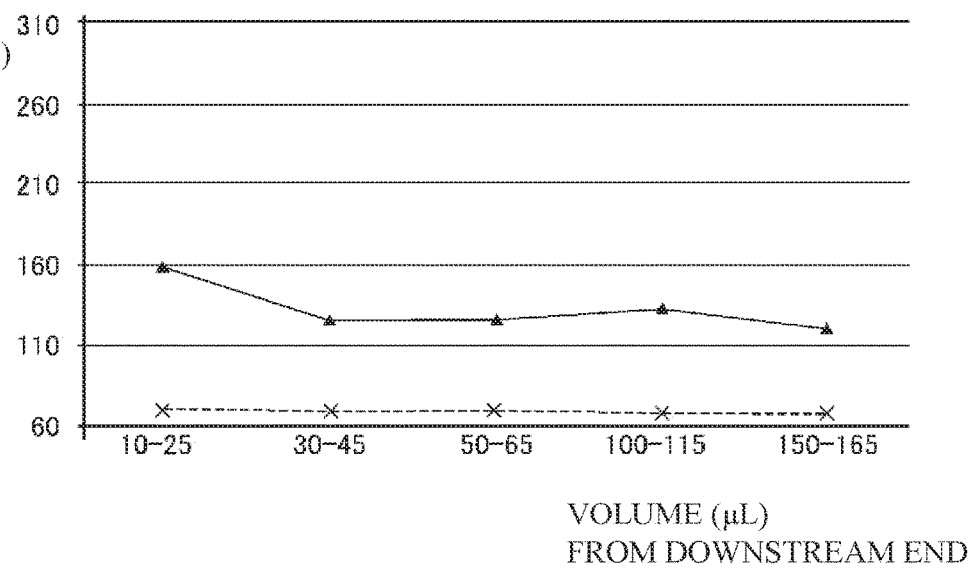
FIG. 8A is a distribution chart of large particles after the biological sample is caused to flow through the liquid flow channel by the biological sample imaging device according to the embodiment of the present invention.
Figure 8B:
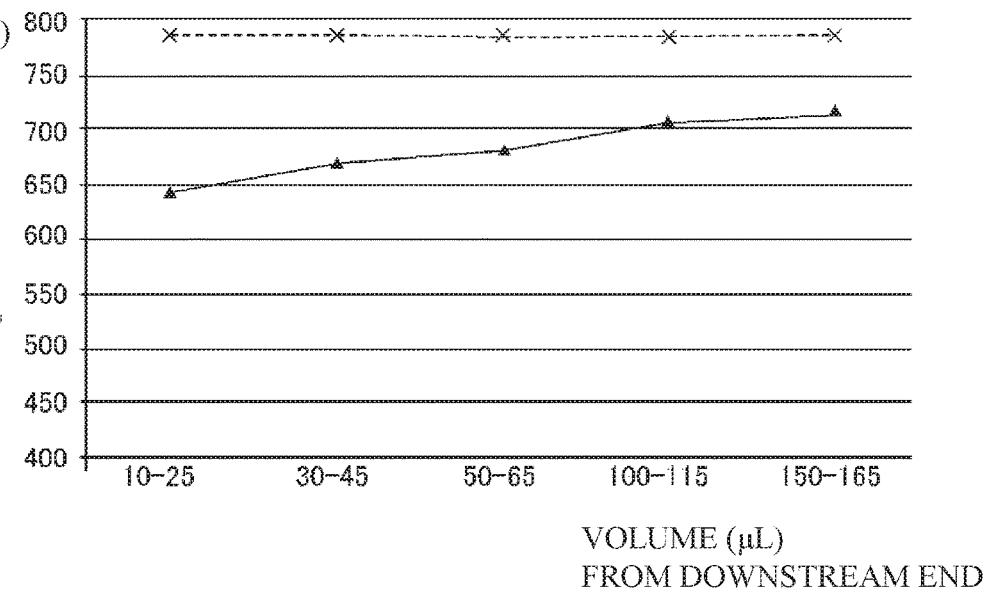
FIG. 8B is a distribution chart of small particles after the biological sample is caused to flow through the liquid flow channel by the biological sample imaging device according to the embodiment of the present invention.

FIG. 8A is a distribution chart of the large particles after the biological sample 104 has been caused to flow through the liquid flow channel 40 by the biological sample imaging device 10. FIG. 8B is a distribution chart of the small particles after the biological sample 104 has been caused to flow through the liquid flow channel 40 by the biological sample imaging device 10. In FIG. 8A, a broken line indicates the number of large particles per unit volume (about 70/µL) that is measured by a flow cytometer. The broken line indicates the number of large particles per unit volume in the sample container 34. As shown in FIG. 8A, after the biological sample 104 has been caused to flow through the liquid flow channel 40, the number of large particles per unit volume is 1.5 times or more at any position within the range of 165 µL from the downstream end 104a of the biological sample 104. Accordingly, it is found that, also within the imaging range, the number of large particles per unit volume is 1.5 times or more as compared with the original number of large particles per unit volume.

In FIG. 8B, a broken line indicates the number of small particles per unit volume (about 790/µL) that is measured by a flow cytometer. It is found that 80% or more is ensured as compared with the original number of small particles per unit volume.

According to the aforementioned biological sample imaging device 10, the pump controller 20c causes the syringe pump 24 to perform the first operation, whereby large particles such as the epithelial cells 114 and the urinary casts 116 can be concentrated around the downstream end 104a of the biological sample 104. Thereafter, the pump controller 20c causes the syringe pump 24 to perform the second operation, whereby the large particles concentrated around the downstream end 104a of the biological sample 104 can be dispersed to the upstream side. The inner space 14e of the imaging cell 14 is filled with the biological sample 104 that has been caused to forwardly and reversely flow through the liquid flow channel 40. Therefore, a sufficient number of large particles are present in the imaging cell 14, and moreover, these large particles are moderately dispersed, whereby the individual large particles can be reflected in images taken by the camera 18. As a result, the accuracy of the urine test can be improved.

Of the large particles in the urine sample whose images are taken by the biological sample imaging device 10, the epithelial cells 114 appear in urine due to damage of a kidney or the urinary tract, and images thereof are important information for judging which portion of the kidney or urinary tract is damaged and the extent of the damage. For example, the images of the epithelial cells 114 are used for diagnosis of diseases such as cystitis and urethritis. The urinary casts 116 appear in urine when a renal tubular lumen is temporarily closed and thereafter urine flows again, and images thereof are also important information for judging which portion of the kidney or urinary tract is abnormal and the extent of the abnormality. For example, the images of the urinary casts 116 are used for diagnosis of diseases such as chronic nephritis, glomerulonephritis, pyelonephritis, and nephrotic syndrome. Generally, only a small number of large particles such as the epithelial cells 114 and the urinary casts 116 are contained in a urine sample. However, even a small number of large particles provide clinically very important findings as described above. According to the biological sample imaging device 10, the large particles in the urine sample, which provide such important findings, can be efficiently reflected in images so as not to overlap each other, through the aforementioned concentration and dispersion processes. Thus, according to the present embodiment, the reliability of the urine test can be significantly improved.

The present invention is not limited to the above embodiment. Various modifications of the above embodiment can be made, and these modifications are also within the scope of the present invention. For example, while the first sensor 28a and the second sensor 28b are used in the above description, these sensors are not necessarily required for controlling the position of the downstream end 104a of the biological sample 104.

Figure 9A:
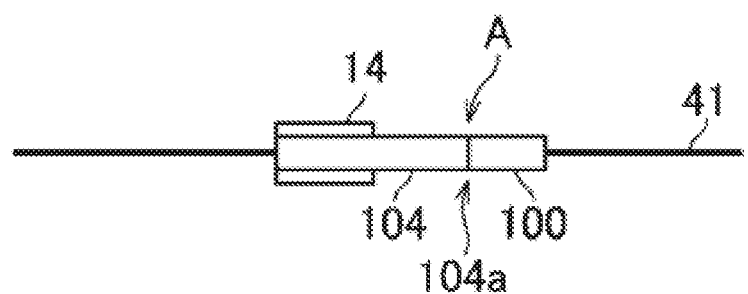
FIG. 9A is a diagram showing another example of pump control by the biological sample imaging device according to the embodiment of the present invention.
Figure 9B:
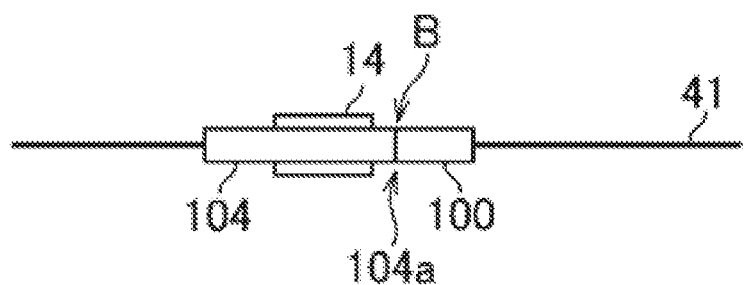
FIG. 9B is a diagram showing another example of pump control by the biological sample imaging device according to the embodiment of the present invention.

The third operation by the pump controller 20c is not necessarily required. That is, as shown in FIGS. 9A and 9B, the first position A may be provided on the downstream side relative to the imaging range of the imaging cell 14, and the second position B may be provided at the downstream end of the imaging range of the imaging cell 14 or on the downstream side relative to the downstream end. In this case, the inner space 14e of the imaging cell 14 is filled with the biological sample 104 immediately after the second operation has been performed. Thus, the time interval from start of suction of the biological sample 104 to image-taking by the camera 18 can be reduced.

The biological sample imaging device and the biological sample imaging method according to the present invention can be favorably used for, for example, image-taking of a liquid biological sample containing particles, such as urine and blood.

While the present invention has been described in detail, the foregoing description is in all aspects illustrative and not restrictive. It will be understood that numerous other modifications and variations can be devised without departing from the scope of the present invention.

What is claimed is:

1. A biological sample imaging device comprising:
   a liquid flow channel through which a liquid biological sample containing particles flows, the liquid flow channel having, at a predetermined position, an imaging range within which images of the particles contained in the biological sample are taken, wherein the particles include a first type of particles and a second type of particles having a larger size than the first type of particles;
   a pump configured to cause the biological sample, which has been introduced from a container into the liquid flow channel, to flow in a forward direction from an upstream side toward a downstream side or in a direction reverse to the forward direction;
   a pump controller configured to cause the pump to perform a first operation of causing the biological sample introduced into the liquid flow channel to flow in the forward direction until the biological sample reaches a first position that is upstream relative to the imaging range, a second operation of causing the biological sample to flow in the reverse direction, and a third operation of causing the biological sample to flow in the forward direction until the biological sample is within the imaging range; and
   an imaging unit configured to take, within the imaging range, images of the particles contained in the biological sample after the particles are precipitated at a bottom of the liquid flow channel after a predetermined amount of time following the third operation, wherein both the first type of particles and the second type of particles remain together in the liquid flow channel.

2. The biological sample imaging device of claim 1, further comprising:

a first determination unit configured to determine that a downstream end of the biological sample introduced into the liquid flow channel has reached a first position in the liquid flow channel; and a second determination unit configured to determine that the downstream end of the biological sample introduced into the liquid flow channel has reached a second position on an upstream side relative to the first position in the liquid flow channel, wherein the pump controller causes the downstream end of the biological sample to reach the first position through the first operation, and causes the downstream end of the biological sample to reach the second position through the second operation.

3. The biological sample imaging device of claim 1, wherein the pump controller, in the third operation, causes the downstream end of the biological sample to reach a downstream side relative to the imaging range, and the imaging unit takes the images of the particles contained in the biological sample present within the imaging range, with the downstream end of the biological sample being present on the downstream side relative to the imaging range.

4. The biological sample imaging device of claim 1, wherein the third operation is performed, with the upstream end of the liquid flow channel being pulled up from a liquid surface in the container.

5. The biological sample imaging device of claim 2, wherein the first position is provided on the downstream side relative to the imaging range, and the second position is provided at the downstream end of the imaging range or on the downstream side relative to the downstream end.

6. The biological sample imaging device of claim 2, wherein the first determination unit determines that the downstream end of the biological sample has reached the first position, on the basis of a suction amount or a discharge amount of the pump.

7. The biological sample imaging device of claim 2, wherein the second determination unit determines that the downstream end of the biological sample has reached the second position, on the basis of a suction amount or a discharge amount of the pump.

8. The biological sample imaging device of claim 2, further comprising a first sensor configured to output data according to a type of an object that flows through the liquid flow channel, wherein the first determination unit determines that the downstream end of the biological sample has reached the first position, on the basis of the data outputted from the first sensor.

9. The biological sample imaging device of claim 8, further comprising a second sensor configured to output data according to the type of the object that flows through the liquid flow channel, wherein a detection position, by the second sensor, of the object that flows through the liquid flow channel is provided on the upstream side relative to the detection position of the first sensor in the liquid flow channel.

10. The biological sample imaging device of claim 2, wherein an internal capacity of the liquid flow channel from the upstream end of the liquid flow channel to the second position is greater than an internal capacity of the liquid flow channel at least within the imaging range.

11. The biological sample imaging device of claim 1, wherein the liquid flow channel includes: a suction nozzle configured to suck the biological sample; an imaging cell having an inner space to be filled with the biological sample; and a tube configured to supply, to the imaging cell, the biological sample sucked by the suction nozzle, the imaging cell has a space region, sandwiched by opposing thin plate parts, into which the biological sample is introduced, and the imaging range is provided in an entirety or a part of the space region.

12. The biological sample imaging device of claim 11, wherein an interval between the thin plate parts is shorter than at least one of inner diameters of the tube and the suction nozzle.

13. The biological sample imaging device of claim 1, wherein the biological sample is urine.

14. The biological sample imaging device of claim 1, wherein the first operation includes: a liquid introducing operation of introducing the biological sample into the liquid flow channel from an upstream end of the liquid flow channel; and an air introducing operation of introducing air into the liquid flow channel from the upstream end of the liquid flow channel after the liquid introducing operation.

15. The biological sample imaging device of claim 9, wherein the first operation includes: a liquid introducing operation of introducing the biological sample into the liquid flow channel from an upstream end of the liquid flow channel; and an air introducing operation of introducing air into the liquid flow channel from the upstream end of the liquid flow channel after the liquid introducing operation, the biological sample imaging device further comprising an abnormality determination unit configured to determine that the biological sample introduced into the liquid flow channel through the liquid introducing operation is insufficient, when air is detected by the second sensor during a monitoring period provided after start of the air introducing operation.

16. The biological sample imaging device of claim 14, wherein the second operation is performed, with the upstream end of the liquid flow channel being pulled up from a liquid surface in the container.

17. The biological sample imaging device of claim 1, further comprising an agitation means configured to agitate the biological sample stored in the container before the first operation.

18. The biological sample imaging device of claim 1, wherein the pump controller causes a plurality of biological samples to be sequentially introduced into the liquid flow channel from a plurality of containers, and causes the pump to perform the first operation and the second operation for each biological sample, and the imaging unit sequentially takes images of the biological samples that are sequentially introduced into the liquid flow channel from the plurality of containers.

19. A biological sample imaging method comprising:

a first step of introducing a biological sample containing particles into a liquid flow channel, wherein the particles include a first type of particles and a second type of particles having a larger size than the first type of particles;

a second step of causing the biological sample introduced into the liquid flow channel to flow in a forward direction from an upstream side toward a downstream side until the biological sample reaches a first position that is upstream relative to an imaging range;

a third step of causing the biological sample to flow in a reverse direction after the second step;

a fourth step of causing the biological sample to flow in the forward direction until the biological sample is within the imaging range; and an imaging step of taking, within the imaging range set on the liquid flow channel, images of the particles contained in the biological sample after the particles are precipitated at a bottom of the liquid flow channel after a predetermined amount of time following the fourth step, wherein both the first type of particles and the second type of particles remain together in the liquid flow channel.

20. The biological sample imaging device of claim 1, wherein:

the first type of particles includes at least one of red blood cells or white blood cells, and the second type of particles includes at least one of epithelial cells or urinary casts.

* * * * *